US011102381B1

United States Patent
Alambeigi et al.

(10) Patent No.: US 11,102,381 B1
(45) Date of Patent: Aug. 24, 2021

(54) METHODS, SYSTEMS AND CONTROLLERS FOR FACILITATING CLEANING OF AN IMAGING ELEMENT OF AN IMAGING DEVICE

(71) Applicants: BOARD OF REGENTS, THE UNIVERSITY OF TEXAS SYSTEM, Austin, TX (US); ClearCam Inc., Austin, TX (US)

(72) Inventors: Farshid Alambeigi, Austin, TX (US); Alexander Cohen, Austin, TX (US); Christopher R. Idelson, Austin, TX (US); Christopher Rylander, Austin, TX (US)

(73) Assignee: BOARD OF REGENTS, THE UNIVERSITY OF TEXAS SYSTEM CLEARCAM INC., Austin, TX (US)

( * ) Notice: Subject to any disclaimer, the term of this patent is extended or adjusted under 35 U.S.C. 154(b) by 0 days.

(21) Appl. No.: 17/141,428

(22) Filed: Jan. 5, 2021

(51) Int. Cl.
| | |
|---|---|
| *H04N 5/217* | (2011.01) |
| *G06T 7/00* | (2017.01) |
| *A61B 1/313* | (2006.01) |
| *A61B 34/37* | (2016.01) |
| *A61B 1/12* | (2006.01) |
| *A61B 1/00* | (2006.01) |
| *A61B 34/00* | (2016.01) |
| *A61B 34/30* | (2016.01) |

(52) U.S. Cl.
CPC ......... *H04N 5/217* (2013.01); *A61B 1/00006* (2013.01); *A61B 1/126* (2013.01); *A61B 1/3132* (2013.01); *A61B 34/25* (2016.02); *A61B 34/37* (2016.02); *G06T 7/0002* (2013.01); *A61B 2034/302* (2016.02); *G06T 2207/30168* (2013.01)

(58) Field of Classification Search
CPC ........ H04N 5/217; A61B 34/25; A61B 34/37; A61B 1/00006; A61B 1/126; A61B 1/3132; G06T 7/0002
See application file for complete search history.

(56) References Cited

U.S. PATENT DOCUMENTS

| | | | |
|---|---|---|---|
| 6,496,257 B1 * | 12/2002 | Taniguchi | G03F 7/2002 355/30 |
| 6,791,608 B1 | 9/2004 | Miyazawa et al. | |
| 6,940,554 B2 | 9/2005 | Robins et al. | |
| 9,083,864 B2 | 7/2015 | Reed et al. | |

(Continued)

*Primary Examiner* — Peter D Le
(74) *Attorney, Agent, or Firm* — Parker Highlander PLLC (57) ABSTRACT

Disclosed herein are technological solutions that are configured to limit sub-optimal visualization of the surgical field during robotic and manual laparoscopic surgery. Such technological solutions are configured to systematically assess cleanliness of an imaging element of a laparoscope (or other type of similar imaging apparatus) and take action for enabling or causing the imaging element to be cleaned. In preferred embodiments, assessment of the cleanliness of the imaging element provides information that can be used for enabling or causing cleaning of the imaging element to be performed in-vivo in either a manual, semi-autonomous or autonomous manner. In this manner such technological solutions advantageously enable the surgical field during surgery to be more efficiently and consistently maintained in an optimal condition.

28 Claims, 5 Drawing Sheets

(56) References Cited

U.S. PATENT DOCUMENTS

| | | | |
|---|---|---|---|
| 9,592,095 | B2 | 3/2017 | Panescu et al. |
| 10,334,227 | B2 | 6/2019 | Panescu et al. |
| 10,398,521 | B2 | 9/2019 | Itkowitz et al. |
| 10,548,459 | B2 | 2/2020 | Debiez et al. |
| 10,678,259 | B1* | 6/2020 | Ferguson ................ G06T 7/001 |
| 10,799,090 | B1* | 10/2020 | Venkataraman ... A61B 1/00036 |
| 10,842,575 | B2 | 11/2020 | Eom et al. |
| 10,868,984 | B1* | 12/2020 | Charlton ................ H04N 5/341 |
| 2001/0007919 | A1* | 7/2001 | Shahidi ................. A61B 5/064 600/427 |
| 2003/0013949 | A1* | 1/2003 | Moll ...................... A61B 34/35 600/407 |
| 2003/0029464 | A1* | 2/2003 | Chen ..................... A61B 90/36 600/429 |
| 2003/0193604 | A1 | 10/2003 | Robins et al. |
| 2005/0129394 | A1* | 6/2005 | Ichikawa ............... G03B 17/48 396/429 |
| 2005/0228231 | A1* | 10/2005 | MacKinnon ........... A61B 1/227 600/180 |
| 2006/0069306 | A1* | 3/2006 | Banik ................... A61B 1/0008 600/118 |
| 2008/0158555 | A1 | 7/2008 | Mori et al. |
| 2009/0171160 | A1* | 7/2009 | Ito ....................... A61B 1/0055 600/141 |
| 2009/0278950 | A1 | 11/2009 | Deng et al. |
| 2010/0010310 | A1* | 1/2010 | Weisenburgh, II .... A61B 1/126 600/156 |
| 2010/0182450 | A1 | 7/2010 | Kumar et al. |
| 2012/0059222 | A1* | 3/2012 | Yoshida ............. A61B 1/00091 600/157 |
| 2012/0081556 | A1* | 4/2012 | Hwang .............. H04N 1/32037 348/207.1 |
| 2012/0101337 | A1* | 4/2012 | Clark .................... A61B 1/121 600/157 |
| 2012/0101338 | A1* | 4/2012 | O'Prey ................. A61B 1/126 600/157 |
| 2013/0071004 | A1* | 3/2013 | Yonezawa ............ G06K 9/0061 382/133 |
| 2013/0331730 | A1* | 12/2013 | Fenech ............. A61B 1/00091 600/560 |
| 2014/0350373 | A1* | 11/2014 | Pugh ..................... A61B 3/101 600/367 |
| 2014/0371528 | A1* | 12/2014 | Yen ................... G02B 23/2476 600/109 |
| 2016/0004144 | A1* | 1/2016 | Laroia ................. H04N 5/2258 348/222.1 |
| 2016/0113484 | A1* | 4/2016 | Nakaguchi ......... A61B 1/00048 600/103 |
| 2016/0234405 | A1 | 8/2016 | Yuesheng et al. |
| 2017/0186147 | A1* | 6/2017 | He ....................... G06T 7/0002 |
| 2017/0206657 | A1* | 7/2017 | Nozato ................ G06K 9/4642 |
| 2018/0096474 | A1 | 4/2018 | Guerreiro et al. |
| 2018/0154406 | A1* | 6/2018 | Magee ............... G02B 27/0006 |
| 2019/0053861 | A1* | 2/2019 | Lwin ..................... A61B 1/05 |
| 2019/0102876 | A1* | 4/2019 | Sanders ................ G01N 21/78 |
| 2019/0152447 | A1 | 5/2019 | Hansen et al. |
| 2019/0351873 | A1 | 11/2019 | Dalal et al. |

\* cited by examiner

METHODS, SYSTEMS AND CONTROLLERS FOR FACILITATING CLEANING OF AN IMAGING ELEMENT OF AN IMAGING DEVICE

FIELD OF THE DISCLOSURE

The disclosures made herein relate generally to imaging devices and implements and, more particularly, to methods, systems and controllers for facilitating cleaning of an imaging element of an imaging device.

BACKGROUND

There are many types of operational procedures that require visualization of structures located within an enclosed cavity of a body of material (i.e., a body cavity). Such operational procedures are known to use an imaging device having a portion thereof that is insertable into the body cavity for acquiring imaging information of structures within the body cavity. A prime example such an operational procedure is a surgical procedure that requires imaging within a body cavity of a patient.

It is known that a surgeon's visualization of the surgical field frequently becomes sub-optimal during surgery within a body cavity (e.g., laparoscopic surgery), thereby requiring cleaning of the imaging element of the imaging element. Such sub-optimal visualization results from an imaging element (e.g., a lens) of the imaging device (e.g., a laparoscope) becoming contaminated with contaminants (e.g., vapor, liquid and/or solid debris). Such contaminants result in an obscured field of view. One reason for visualization of the surgical field becoming sub-optimal during laparoscopic surgery arises from delayed recognition of such sub-optimal visualization, such as due to the gradual contamination of the imaging element leading to the delayed recognition that the field of view in the surgical field has become diminished to the point where cleaning of the imaging element is required or desired. Another reason for visualization of the surgical field becoming sub-optimal during laparoscopic surgery arises from a surgeon intentionally delaying cleaning of the imaging element to preclude interruption of the surgical procedure, particularly when cleaning is performed outside of the body cavity—i.e., ex-vivo. Such issues may lead to wasted time, frustrated clinicians, or even harmful patient outcomes.

To date, the most prevalent approaches for cleaning such contaminants from the surface of the imaging element are performed ex-vivo after removing the imaging element of the laparoscope from the surgical field. These ex-vivo cleaning approaches are known to often be less than desirable, as they are inefficient, frustrating, and can introduce adverse considerations relative to patient safety and medical outcomes.

Devices and techniques for in-vivo cleaning of the imaging element are known. These devices and techniques have attempted to address imaging element considerations using a variety of approaches. One such approach comprises the use of pneumatic or liquid irrigation to clear the imaging element of contaminants. Another such approach comprises the use of mechanical wiping methods, such as via a wiper, absorbent pad or the like. These approaches have relied upon surgical staff (e.g., a surgeon, nurse, etc.) to make a visual determination during a surgical procedure as to when obstruction of the field of view has become significant enough to require cleaning of the imaging element during the surgical procedure.

Therefore, a technological solution that is configured facilitating cleaning of an imaging element of an imaging device to limit sub-optimal visualization within an enclosed cavity of a body of material (e.g., a surgical field during laparoscopic surgery) would be beneficial, desirable and useful.

SUMMARY OF THE DISCLOSURE

Embodiments of the disclosures made herein are directed to technological solutions that are configured to facilitating cleaning of an imaging element of an imaging device to limit sub-optimal visualization within an enclosed cavity of a body of material. A surgical field during robotic and manual laparoscopic surgery is an example of such an enclosed cavity of a body of material. In some embodiments, the disclosures herein are directed to technological solutions that are configured to systematically assess cleanliness of an imaging element of an imaging device (e.g., laparoscope or other type of similar imaging apparatus) and take action for enabling and/or causing the imaging element to be cleaned. In preferred embodiments, assessment of the cleanliness of the imaging element provides information that can be used for enabling and/or causing cleaning of the imaging element to be performed in-vivo in either a manual, semi-autonomous or autonomous manner. For example, in general terms, technological solutions in accordance with embodiments of the disclosures made herein link actuation and/or recommendation of an imaging element cleaning operation to a quantified and/or qualified metric characterizing cleanliness of the imaging element and/or to a user's image clarity preference. Accordingly, technological solutions in accordance with embodiments of the disclosures made herein advantageously enable visualization of a structure within an enclosed cavity of a body of material, whether a surgical field during surgery or otherwise, to be more efficiently and consistently maintained in a preferred (e.g., optimal) condition.

In one embodiment of the disclosures made herein, a computer-assisted system comprises an imaging device, a cleaning device attached to the imaging device and one or more processors coupled to the imaging device and the cleaning device. The imaging device has an imaging element through which image information of an anatomical structure within a body cavity is acquired during a surgical procedure. The cleaning device is adapted to clean a surface of the imaging element in response to activation thereof. The one or more processors are configured to process a portion of the image information to determine cleanliness of the imaging element and, after a determination of the imaging element exhibiting unacceptable cleanliness is made, cause the cleaning device to perform one or more instances of an imaging element cleaning operation.

In one or more embodiments, a robotic surgical system comprises an imaging apparatus, a control console and a processing unit. The imaging apparatus includes an imaging device and a cleaning device. The imaging device comprises an imaging element for acquiring image information from a surgical field within a body cavity during a surgical procedure. The cleaning device is adapted to clean a surface of the imaging element in response to activation thereof while the imaging element is within the body cavity. The control console includes a visual display device adapted to have the image information displayed thereon. The processing unit is coupled to the imaging apparatus and the control console. The processing unit comprises one or more processors configured to process a portion of the image information to determine when the imaging element exhibits unacceptable cleanliness and, in response to a determination that the imaging element exhibits unacceptable cleanliness, cause one or more responsive actions to be implemented by at least one of the cleaning device and the imaging apparatus controller. Each of the responsive actions at least one of cause the cleaning device to clean the imaging element through use of at least one of the cleaning device and the visual display device and enable the cleaning device to clean the imaging element through use of at least one of the cleaning device and the visual display device.

In one or more embodiments, a non-transitory machine-readable medium comprises a plurality of machine-readable instructions which when executed by one or more processors associated with a computer assisted system are adapted to cause the one or more processors to perform a method comprising a plurality of processes. A process is performed for receiving image information depicting an anatomical structure within a body cavity of a surgical patient. The image information is acquired by an imaging element of an imaging device having a cleaning device attached thereto. Actuation of the cleaning device causes the cleaning device to perform one or more instances of an imaging element cleaning operation. A process is performed for deriving, from a portion of the image information, information characterizing cleanliness of the imaging element. In response the cleanliness characterizing indicating that the imaging element exhibits unacceptable cleanliness, a process is performed for causing one or more responsive actions to be performed. The responsive actions include actuating the cleaning device, outputting a signal enabling an indicator of cleanliness of the imaging element to be displayed on a visual display device and enabling operation of the cleaning device to be selectively actuated.

In one or more embodiments, an image information processor is adapted for use with an in-vivo imaging apparatus. The image information processor has a computer-readable non-transitory medium carrying one or more sequences of instructions to process the image information. Execution of the one or more sequences of instructions by one or more processors causes the one or more processors to perform a plurality of processes. A process is performed for receiving image information acquired by an imaging element of the in-vivo imaging apparatus. The received image information corresponds to a surgical field visible by the imaging element and enables the surgical field to be viewed at a location remote from the surgical field. A process is performed for deriving, from the received image information, information characterizing cleanliness of the imaging element. A process is performed for generating a responsive action signal corresponding to the derived information. A process is performed for transmitting the responsive action signal for reception by the in-vivo imaging apparatus to enable an imaging surface of the imaging element to be cleaned by a cleaning device of the in-vivo imaging apparatus based upon the derived information.

In another embodiment of the disclosures made herein, an imaging element assessment apparatus for use with an in-vivo imaging apparatus comprises an image information receiver and an image information processor coupled to the image information receiver for enabling the received image information to be processed by the image information processor. The image information receiver is adapted for being coupled to the in-vivo imaging apparatus to receive image information acquired by an imaging element of the in-vivo imaging apparatus. The image information enables a surgical field visible by the imaging element to be viewed at a location remote from the surgical field. The image information processor is coupled to the image information receiver for enabling processing of the received image information by the image information processor. Such processing comprises execution of one or more sequences of instructions to process the received image information. Execution of the one or more sequences of instructions causes one or more instruction processors to perform a plurality of processes. A process is performed for deriving, from the received image information, information characterizing cleanliness of the imaging element. A process is performed for generating a responsive action signal corresponding to the derived information. A process is performed for transmitting the responsive action signal for reception by the in-vivo imaging apparatus to enable an imaging surface of the imaging element to be cleaned by a cleaning device of the in-vivo imaging apparatus based upon the derived information.

In another embodiment of the disclosures made herein, a laparoscopic surgery system comprises a surgical imaging apparatus, an instrument control console coupled to the in-vivo surgical imaging and an imaging element assessment apparatus coupled to the instrument control console. The instrument control console receives image information acquired by an imaging element of the surgical imaging apparatus. The received image information enables a surgical field visible by the imaging element to be viewed on a visual display device of the instrument control console. The imaging element assessment apparatus accesses the received image information from the instrument control console. The imaging element assessment apparatus comprises an image information processor for processing the received image information by performing execution of one or more sequences of instructions. Execution of the one or more sequences of instructions causes one or more instruction processors to perform a plurality of processes. A process is performed for deriving, from the received image information, information characterizing cleanliness of the imaging element. An operation is performed for generating a responsive action signal corresponding to the derived information. An operation is performed for transmitting the responsive action signal to a device adapted to cause and/or enable an imaging surface of the imaging element to be cleaned by a cleaning device of the in-vivo surgical imaging apparatus and/or to cause and/or enable information characterizing cleanliness of the imaging element to be displayed on the visual display device.

In one or more embodiments, the one or more processors being configured to process the portion of the image information includes the one or more processors being configured to one of quantitatively characterize cleanliness of the imaging element based at least partially upon the portion of the image information and qualitatively characterize cleanliness of the imaging element based at least partially upon the portion of the image information.

In one or more embodiments, the portion of the image information includes an image of an anatomical structure within a body cavity.

In one or more embodiments, the one or more processors being configured to process the portion of the image information includes the one or more processors being configured to correlate an image to one or more visual clarity scored reference images each having a respective visual clarity determined to be visually equivalent to the image.

In one or more embodiments, each of the scored reference images has a score one of rating cleanliness of an imaging element used for acquiring a respective one of the reference images and ranking cleanliness of an imaging element used for acquiring a respective one of the reference images.

In one or more embodiments, the computer-assisted system comprises a visual display device.

In one or more embodiments, the one or more processors being configured to process the portion of the image information includes the one or more processors being configured to correlate visual clarity of portion of the image information to one or more visual clarity scored reference images and, based at least partially on the score of one or more of the correlated reference images, determine a metric characterizing cleanliness of the imaging element.

In one or more embodiments, the one or more processors are further configured to cause the metric to be displayed on a visual display device.

In one or more embodiments, the one or more processors are further configured to cause a visual indictor characterizing cleanliness of the imaging element to be displayed on a visual display device in response to a determination of the imaging element exhibiting unacceptable cleanliness being made.

In one or more embodiments, the one or more processors are configured to enable a particular user of the imaging device to select one or more visual clarity reference images exhibiting acceptable visual clarity.

In one or more embodiments, the one or more processors being configured to process one or more of the image information includes the one or more processors being configured to use the selected visual clarity reference images to determine when the imaging element exhibits unacceptable cleanliness for the particular user.

In one or more embodiments, the one or more processors being configured to cause the cleaning device to perform one or more instances of an imaging element cleaning operation includes the one or more processors being configured to transmit one or more actuation signals for reception by the cleaning device.

In one or more embodiments, the one or more processors being configured to cause the cleaning device to perform one or more instances of an imaging element cleaning operation includes the one or more processors being configured to issue a request for approval by a human user to initiate cleaning of the imaging element by the cleaning device and, in response to receiving approval to the request, actuate the cleaning device.

In one or more embodiments, the received image information includes at least one digital image of the surgical field and deriving the cleanliness characterizing information includes generating a score correlating clarity of the at least one digital image to cleanliness of the imaging element.

In one or more embodiments, generating the clarity correlating score includes accessing a dataset of surgical field reference images each having a score correlating end-user visualization of a surgical field depicted in a respective one of the reference images to a degree of cleanliness of an imaging element through which the respective one of the reference images was acquired.

In one or more embodiments, generating the clarity correlating score includes digitally comparing attributes of visible content of at least one image acquired during a surgical procedure to attributes of visible content of one or more of surgical field reference images.

In one or more embodiments, generating the clarity correlating score includes identifying, as a function of the attributes of visible content, one or more of the surgical field reference images exhibiting attributes of visible content most closely matching the attributes of visible content of the at least one image acquired during a surgical procedure.

In one or more embodiments, generating the clarity correlating score includes computing the clarity correlating score as a function of the end-user visualization score of the one or more of the surgical field reference images exhibiting attributes of visible content most closely matching the attributes of visible content of the at least one image acquired during a surgical procedure.

In one or more embodiments, generating the responsive action signal includes generating an actuation signal as a function of the clarity correlating score.

In one or more embodiments, transmitting the responsive action signal includes transmitting the actuation signal for reception by the in-vivo imaging apparatus to cause the cleaning device to clean the imaging element after the in-vivo imaging apparatus receives the actuation signal.

In one or more embodiments, generating the responsive action signal includes generating a score representation signal as a function of the clarity correlating score.

In one or more embodiments, transmitting the responsive action signal includes transmitting the score representation signal for reception by a content output device adapted for outputting a visual score depiction derived from the score representation signal in response to receiving the score representation signal.

These and other objects, embodiments, advantages and/or distinctions of the present invention will become readily apparent upon further review of the following specification, associated drawings and appended claims.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
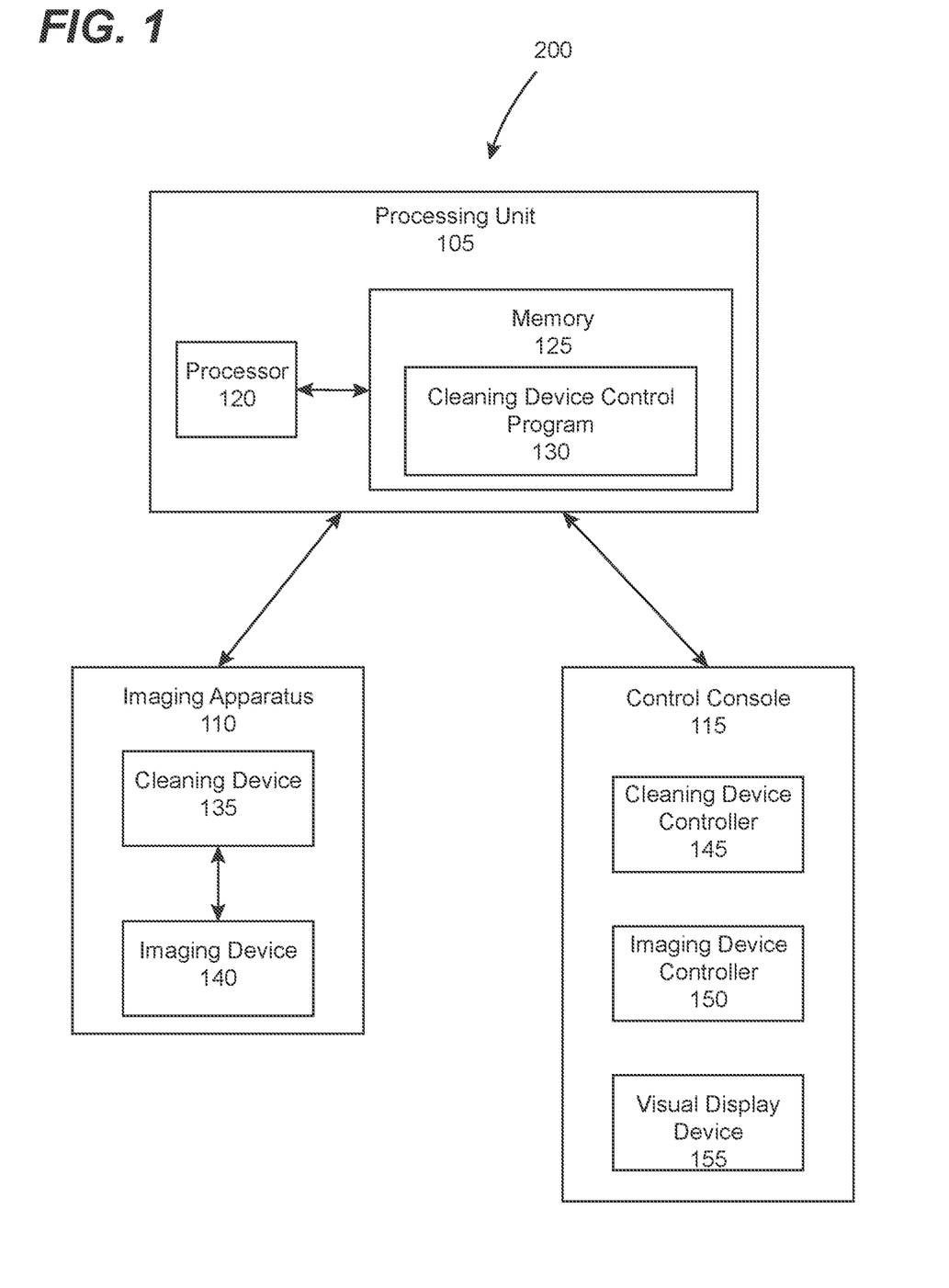
FIG. 1 is a block diagram view showing a computer-assisted system according to one or more embodiment of the disclosures made herein.

FIG. 1 shows a computer-assisted system 100 according to one or more embodiment of the disclosures made herein. The computer-assisted system 100 includes a processing unit 105, an imaging apparatus 110 and a control console 115. The imaging apparatus 110 and the control console 115 may be both operably connected to the processing unit 105 via respective communication interfaces. Such operable connection permits commands, information and data to be communicated (e.g., via digital signals) between the processing unit 105 and the imaging apparatus 110 and between the processing unit 105 and the control console 115. The interface may include one or more cables, circuits, connectors, and/or buses and may further include one or more networks with one or more network switching and/or routing devices.

Processing unit 105 includes a processor 120 coupled to memory 125. Operation of processing unit 105 is controlled by the processor 120. And although the processing unit 105 is shown with only a single processor (i.e., processor 120), it is understood that processor 120 may be representative of one or more central processing units, multi-core processors, microprocessors, microcontrollers, digital signal processors, field programmable gate arrays (FPGAs), application specific integrated circuits (ASICs), and/or the like in processing unit 105. Processing unit 105 may be implemented as a stand-alone subsystem and/or board added to a computing device or as a virtual machine.

Examples of control units, such as the processing unit 105, may include non-transient, tangible, machine-readable media that include executable code that when run by one or more processors (e.g., processor 120) may cause the one or more processors to perform the processes of methods 200, 300 and/or 400. Memory 125 may be used to store a program (i.e., one or more sequences of instructions (e.g., machine-readable) that may be in the form of a software application) executed by the processing unit 105 via the processor 120 thereof and/or one or more data structures used during operation of the processing unit 105. Memory 125 may include one or more types of machine-readable media. Some common forms of machine-readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read a program (e.g., application software).

As shown, memory 120 includes a cleaning device control program 130 that may be used to support manual, semiautonomous and/or autonomous control of a cleaning device 135 of the imaging apparatus 110. An imaging device 140 of the imaging apparatus 110 includes an imaging element (e.g., lens) that acquires image information (e.g., visually depicted as pictures, video streams, and the like). The cleaning device is adapted to clean a surface of the imaging element in response to activation of the cleaning device 140. The imaging device 140 may be adapted for a particular type of procedure or surgery technique—e.g., endoscope for endoscopic surgery, laparoscope for laparoscopic surgery, and the like. In preferred embodiments, the imaging device 140 may be a laparoscope. The imaging device 140 may be adapted for manual operation or for use in a robotic surgical (i.e., computer-assisted) system.

It is disclosed herein that implements adapted for facilitating cleaning of an imaging element of a surgical device in accordance with the disclosures made herein will be applicable and useful with imaging devices utilized in manual surgical procedures and in robotic surgical procedures. Imaging devices, particularly laparoscopes, are available from, for example, Karl Storz, Linvatec, Olympus, Richard Wolf, Stryker and Intuitive Surgical. Examples of cleaning devices specifically adapted for use with laparoscopes and the like are disclosed in the following US patent publications, all of which are incorporated herein in their entirety by reference: US20090229067, U.S. Ser. No. 10/791,918, U.S. Pat. Nos. 9,050,036, 8,979,738, 7,959,561, 6,923,759 and 6,755,782.

In one or more embodiments, the imaging apparatus 110 may be an in-vivo imaging apparatus whereby the imaging device 140 is used to acquire image information of an in-vivo surgical field that is visible to the imaging element of the imaging device 140—e.g., an anatomical structure within a body cavity is acquired during a surgical procedure. The image information may enable the surgical field to be viewed at a location remote from the surgical field and may enable manual, semi-autonomous and/or autonomous actuation of the cleaning device 135. The cleaning device 135 is coupled to the imaging device 140 of the imaging apparatus 110 for enabling the imaging element to be cleaned such as by any number or cleaning approaches—e.g., wiping, spraying or the like.

The cleaning device control program 130 may include one or more application programming interfaces (APIs) for receiving position, motion, and/or other information from cleaning device 110, for actuating the cleaning device 110, for exchanging position, motion, and/or collision avoidance information related to the imaging device 140 and the like. Although the cleaning device control program 130 is depicted as a program, the cleaning device control program 130 may be implemented using hardware, software, a combination of hardware and software and/or firmware or the like.

The cleaning device control program 130 may be coupled to the imaging apparatus control unit 115 via the aforementioned interface between the processing unit 105 and the imaging apparatus control unit 115. The control console 115 may be used by an operator (e.g., a surgeon) to cause actuation (i.e., operation) of the cleaning device 135 such as via a cleaning device controller 145 of the imaging apparatus control unit 115, to cause actuation (i.e., operation) of the imaging device 140 such as via an imaging device controller 150 of the imaging apparatus control unit 115 and/or to cause display of at least a portion of the image information on a visual display device 155 (i.e., a content output device) of the control console 115. Such display of the image information can be used to enable the operation of the imaging device 140 (e.g., movement thereof) and/or to cause actuation of the cleaning device 135 (e.g., performing one or more instances of an imaging element cleaning operation). In some embodiments, the processing unit 105, the imaging apparatus 110 and the control console 115 may be that of a robotic surgical system such as that available from, for example, Intuitive Surgical, Zimmer Biomet, Medtronic, Stryker, Siemens Healthineers, Johnson & Johnson, and Auris Health.

In some embodiments, the computer-assisted system 100 may have other configurations and/or architectures. In some examples, the processing unit 105 may be included as part of the imaging apparatus 110, the control console 115 or both. Although computer-assisted system 100 is shown to include only one imaging apparatus 110 and having one imaging device 140, one of ordinary skill would understand that computer-assisted system 100 may include any number of imaging apparatuses and/or imaging devices.

In some embodiments, the processing unit 105 may be an information processing system (e.g., a software-hardware package) that is connected in-line between an existing image device and a visual display device. The visual display 155 may be an integrated component of a surgical in-vivo imaging system, a robotic surgical system, or the like. The in-line connection between the imaging device 140 and the visual display device 155 enables visual content (e.g., responsive action information) generated by the processing unit 105 as a function of image information acquired by the imaging device 140 to be displayed on the visual display device 155 in conjunction all or a portion of the image information acquired by the imaging device 140. For example, the visual content generated by the processing unit 105 may be overlayed or integrated into the image information acquired by the imaging device 140. To this end, such an implementation of the processing unit 105 may include the processing unit 105 accessing (e.g., via a digital or optical source) the image information, saving the image information to memory of or accessible by the processing unit 105 and then outputting a combined data signal comprising all or a portion of the image information acquired by the imaging device 140 in combination with the visual content generated by the processing unit 105.

Figure 2:
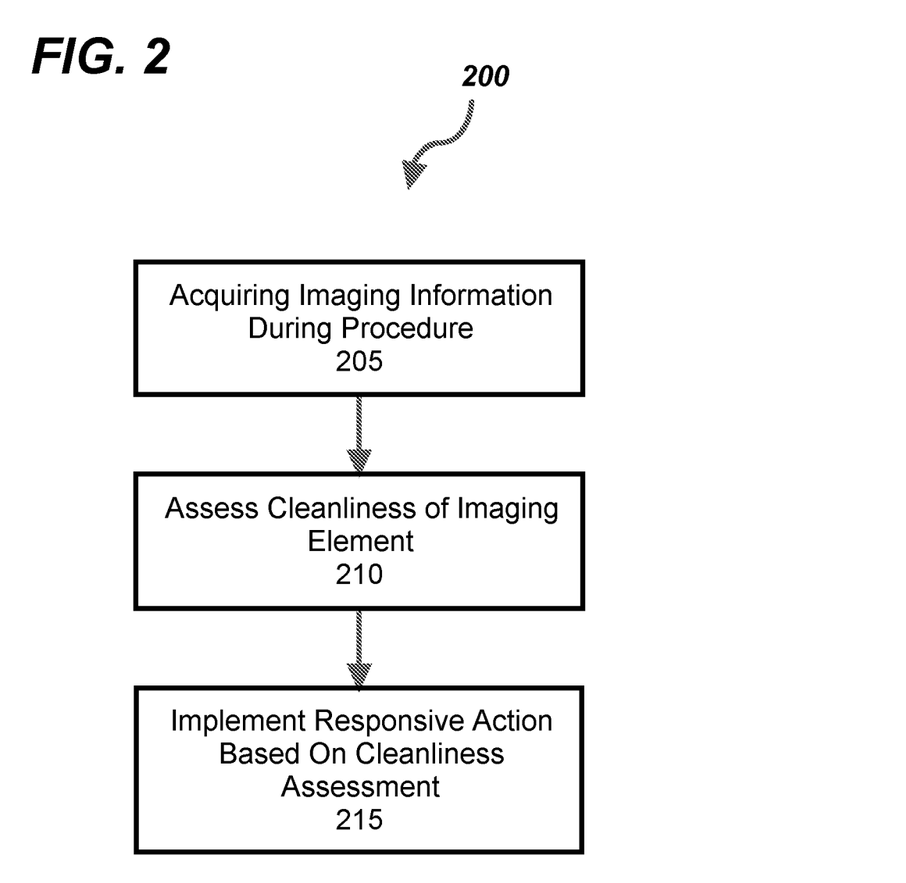
FIG. 2 is a flow diagram view showing a method for performing visual field maintenance procedure in accordance with one or more embodiments of the disclosures herein.

FIG. 2 is a flow diagram view of a method 200 for performing a visual field maintenance procedure in accordance with one or more embodiments of the disclosures herein. In some embodiments, the method 200 may be performed is a surgical procedure implemented manually or robotically using an in-vivo imaging device. The method 200 may be performed by a computer-assisted system in accordance with the disclosures made herein.

In the method 200, a process 205 is performed to acquire image information during a procedure using an imaging device having an imaging element (e.g., a lens) through the image information is acquired—e.g., the imaging device 140 discussed above in reference to FIG. 1. In the case of a surgical procedure, the image information may be acquired via an imaging element of a laparoscope, endoscope or other type of in-vivo imaging device. The image information may be transmitted for reception by a device, system or apparatus that alters the form of the image information—e.g., extracting image frames (e.g., images) from video content, altering resolution of the image information, altering a type of signal comprising the image information and the like.

After or in conjunction with the process 205, a process 210 is performed to assess cleanliness of the imaging element using the image information—e.g., performed by the processor 120 (or processors) discussed above in reference to FIG. 1. Such assessment may include determining and characterizing visual clarity of one or more images derived from image information. In this regard, assessing cleanliness of the imaging element using the image information may include a portion of the image information being processed to determine if the imaging element exhibits unacceptable—e.g., to derive information characterizing cleanliness of the imaging element from a portion (or all) of the image information. For example, all or a portion of the image information may be used to quantitatively characterize cleanliness of the imaging element based at least partially upon the portion of the image information and/or qualitatively characterize cleanliness of the imaging element based at least partially upon the portion of the image information. In some embodiments, processing of the image information may include visual clarity of a portion of the image information (e.g., a video frame) being correlated to one or more visual clarity scored reference images and, based at least partially on the score of one or more of the correlated reference images, a metric characterizing cleanliness of the imaging element (e.g., a score, a ranking, a rating or the like) is determined. In some embodiments, one or more visual clarity reference images exhibiting acceptable visual clarity selected by a particular user of the imaging device may be used in making a determination as to when the imaging element exhibits unacceptable cleanliness for the particular user. Such user-selected images enable determination of the cleanliness of the imaging element to be customized to the imaging element cleanliness preference (e.g., threshold) of a user of the imaging device.

In one or more embodiments, all or a portion of the reference images may be programmatically generated (e.g., computer-generated). For example, a reference image (i.e., image information) may be include programmatically generated "dirt" or other type of imaging element contaminant. An entire dataset of such programmatically generated reference images may be provided and used independently or in combination with a set of reference images captured from a surgical site.

After or in conjunction with the process 210, a process 215 is performed to cause one or more responsive actions to be performed—e.g., performed by the processor 120 (or processors) discussed above in reference to FIG. 1. The responsive actions cause or enable the cleaning device to implement one or more instances of a cleaning operation imaging element in response to or after a determination is made that the imaging element exhibits unacceptable cleanliness. In some embodiments, one or more responsive actions may be performed for indicating that the imaging element exhibits acceptable cleanliness. The responsive actions may be implemented via the cleaning device, a content output device (e.g., the visual display device 155 discussed above in reference to FIG. 1) or a combination thereof. Each of the responsive actions cause the cleaning device to clean the imaging element through use of the cleaning device and/or the visual display device, enable the cleaning device to clean the imaging element through use of the cleaning device and/or the visual display device, or a combination thereof. More specifically, examples of the responsive actions include, but are not limited to, causing the cleaning device to clean the imaging element, causing information related to cleanliness of the imaging element to be outputted (e.g., visually, audibly, otherwise), enabling selective actuation of the cleaning device, and the like.

Methods in accordance with the disclosures made herein and processes thereof may be implemented, at least in part, in the form of executable code (e.g., one or more sequences of instructions). The executable code may be stored on non-transient, tangible, machine-readable media (e.g., the memory 125 of the processing unit 105). When run by one or more processors (e.g., the processor 120 in the processing unit 105), the executable code cause the one or more processors to perform one or more of the processes of the method and, optionally, associated steps thereof. In some embodiments, a method in accordance with the disclosures made herein may be performed by a program (e.g., an application), such as the cleaning device control program 130 of the processing unit 105.

Figure 3A:
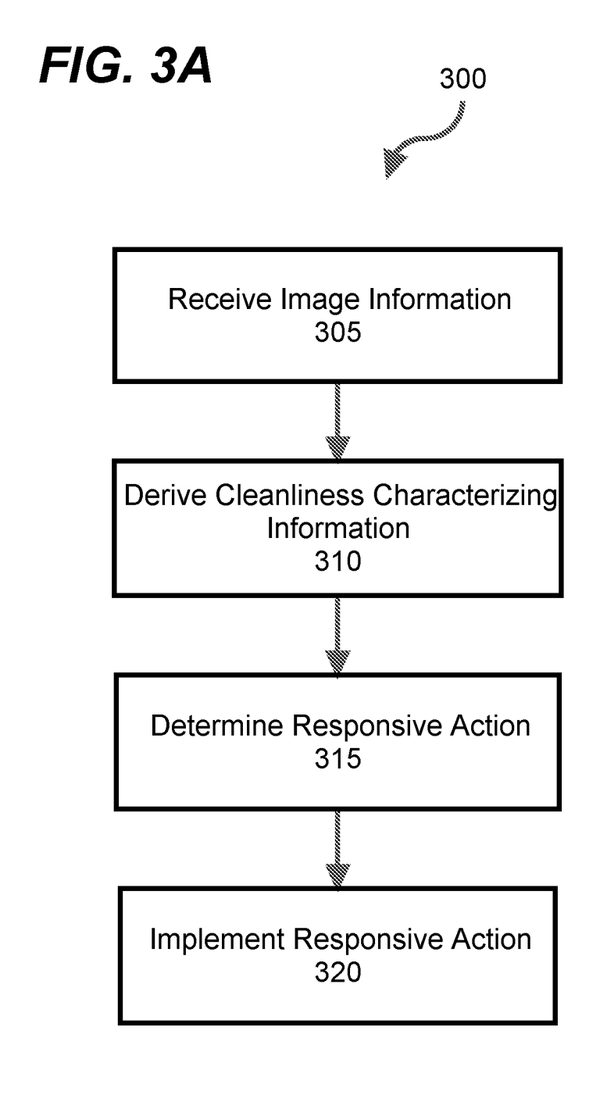
FIG. 3A is a flow diagram view showing a processor-centric method of facilitating imaging element cleaning in accordance with one or more embodiments of the disclosures herein.

FIG. 3A is a processor-centric flow diagram view of a method 300 of facilitating cleaning of an imaging element of a surgical device based upon a derived degree of cleanliness of the imaging element. The method 300 includes a plurality of processes that may be implemented, at least in part, in the form of executable code (e.g., one or more sequences of instructions) stored on non-transient, tangible, machine-readable media that when run by one or more processors (e.g., the processor 120 in the processing unit 105 discussed above in reference to FIG. 1) may cause the one or more processors to perform one or more of the processes of the method 300. In some embodiments, the method 300 may be performed by a program (e.g., an application) such as the cleaning device control program 130. In some embodiments, the method 300 may be used to cause a cleaning device (e.g., cleaning device 135) to clean an imaging element of an imaging device (e.g., the imaging device 140 discussed above in reference to FIG. 1), to cause movement of and/or image capture by an imaging device and/or to cause display (e.g., on the visual display device 155) of at least a portion of the image information and/or information derived from such image information.

At a process 305, image information acquired by an imaging element is received. The received image information corresponds to a surgical field (body cavity scene) visible by the imaging element and may enable the surgical field to be viewed at a location remote. In some embodiments, the image information is all, a portion of, or portions of a stream of video data, which may be generated by a camera connected to or integral with the imaging device (e.g., the imaging element thereof). The image information may be in the form of one or more digital images of the surgical field. For example, one or more discrete images may be generated from a stream of video data (e.g., video frames), may each be captured as still images, or a combination thereof.

At a process 310, information characterizing cleanliness of the imaging element is derived from the received image information. Deriving the cleanliness characterizing information may include generating a score correlating clarity of the received image information (e.g., one or more digital images or segments of video data) to a degree of cleanliness of the imaging element. Correlating clarity of one or more to cleanliness of the imaging element may include associating one or more digital images or segments of video data to a degree of cleanliness selected by a user of the imaging device (e.g., a surgeon), such as by user selection of one or more scored visual clarity reference images. Such association may be performed by a plurality of users such that the clarity correlating score accounts for differentiation of clarity as perceived by different users. The clarity correlating score may be a quantitative characterization, a qualitative characterizing, or other type of characterization.

At a process 315, a responsive action signal corresponding to the derived information is generated. The responsive action signal may include a plurality of separate signal components (e.g., a plurality of signals). The responsive action signal is configured for being utilized by one or more devices to provide an action or operation enabling or causing cleanliness of the imaging element to be improved. To this end, the responsive action signal may include a component (e.g., information) that visually characterizes cleanliness of the imaging element (e.g., a depiction of the clarity correlating score), that is adapted to cause actuation of the cleaning device, or both. In one or more embodiments, the responsive action signal may include an actuation signal that is generated as a function of the clarity correlating score, a score representation signal generated as a function of the clarity correlating score, or both.

At a process 320, the responsive action signal is transmitted for reception by the imaging apparatus to enable an imaging surface of the imaging element to be cleaned by the cleaning device based upon the cleanliness characterizing information. In one or more embodiments, the responsive action signal may be transmitted for reception by the imaging apparatus to cause the cleaning device to clean the imaging element after the imaging apparatus receives the responsive action signal. The responsive action signal may be transmitted for reception by the cleaning device to cause its actuation for cleaning the imaging element, by the visual display device to cause a visual score depiction derived from the responsive action signal to be outputted, or both. To this end, the responsive action signal may include an actuation signal, a score representation signal, or both.

In some embodiments, the response action signal solicits a reply from a user. For example, the response action signal comprises a request for approval to initiate actuation of the cleaning device and, and in response to receiving approval to the request, an actuation signal (i.e., a responsive action signal) is transmitted for reception by the cleaning device for initiating operation of the cleaning device. The request for approval to initiate operation of the cleaning device may be in the form of a selectable displayed graphic whose selection constitutes the approval to initiate operation of the cleaning device. In some embodiments, the response action signal can include a signal component that causes a visual indictor characterizing cleanliness of the imaging element to be displayed on a visual display device in conjunction with the selectable displayed graphic. Separate response action signals (or a multi-component single signal) may also be transmitted for requesting approval to initiate operation of the cleaning device and for causing the visual indictor characterizing cleanliness of the imaging element to be displayed on the visual display device.

Figure 3B:
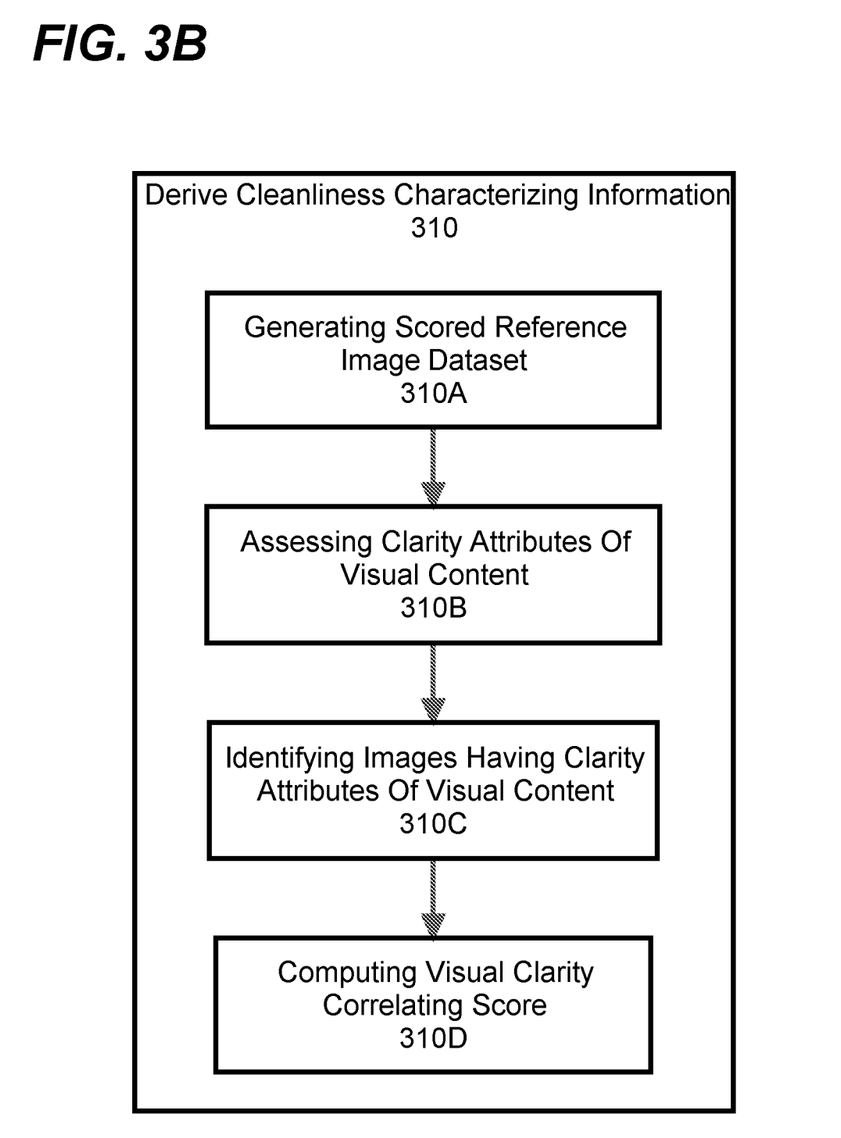
FIG. 3B is a flow diagram view showing a process of generating a clarity correlating score in accordance with one or more embodiments of the disclosures herein.

As disclosed herein, deriving the cleanliness characterizing information may include generating a score correlating clarity of the received image information to a degree of cleanliness of the imaging element. In some embodiments, as depicted in FIG. 3B as process 310A, deriving the cleanliness characterizing information may be include accessing a dataset of reference images (e.g., surgical field reference images) each having a score correlating end-user visualization of a field of view of an imaging element depicted in a respective one of the reference images (i.e., visual clarity) to a degree of cleanliness of an imaging element through which the respective one of the reference images was acquired. In some embodiments, as depicted in FIG. 3B as process 310B, deriving the cleanliness characterizing information may be include assessing clarity attributes of visual content of at least one image in relation to clarity attributes of visual content of one or more of the reference images. In some embodiments, as depicted in FIG. 3B as process 310C, deriving the cleanliness characterizing information may be include identifying, as a function of the clarity attributes of visual content, one or more of the reference images exhibiting clarity attributes of visual content correlating to (i.e., most closely matching) the clarity attributes of visual content of the at least one digital image. In some embodiments, as depicted in FIG. 3B as process 310D of the process 310 to derive the information characterizing cleanliness, deriving the cleanliness characterizing information may be include computing the clarity correlating score as a function of an end-user visualization score of the one or more of the reference images exhibiting clarity attributes of visual content most closely matching clarity attributes of visual content of the at least one digital image.

The dataset of scored reference images can be generated in any number of ways. One such way involves one or more persons each assigning a qualitative rating to each of reference image of the data set. For example, the one or more persons may assign a respective one of a set of available clarity ratings (e.g., Unacceptably Dirty, Acceptably Dirty, Clean) or clarity rankings (e.g., 0-100, where 100 is the clearest) to each reference image of the dataset (or a subset thereof). For each person, a set of scored reference images is produced and compiling such individual sets of scored reference images may be performed to generate a compiled set of data (i.e., a dataset) of scored reference images. Another such way is to generate a set of scored reference images is by monitoring cleaning of an imaging element during a procedure, recording one or more images acquired immediately prior to such cleaning and denoting such images accordingly (e.g., Unacceptably Dirty). Optionally, one or more images at a designated period of time before such cleaning can be denoted accordingly (e.g., Clean or Acceptably Clean). In some embodiments, the processor-based learning structure is a neural network or the like, which may be used for analyzing, organizing and scoring reference images.

Figure 4:
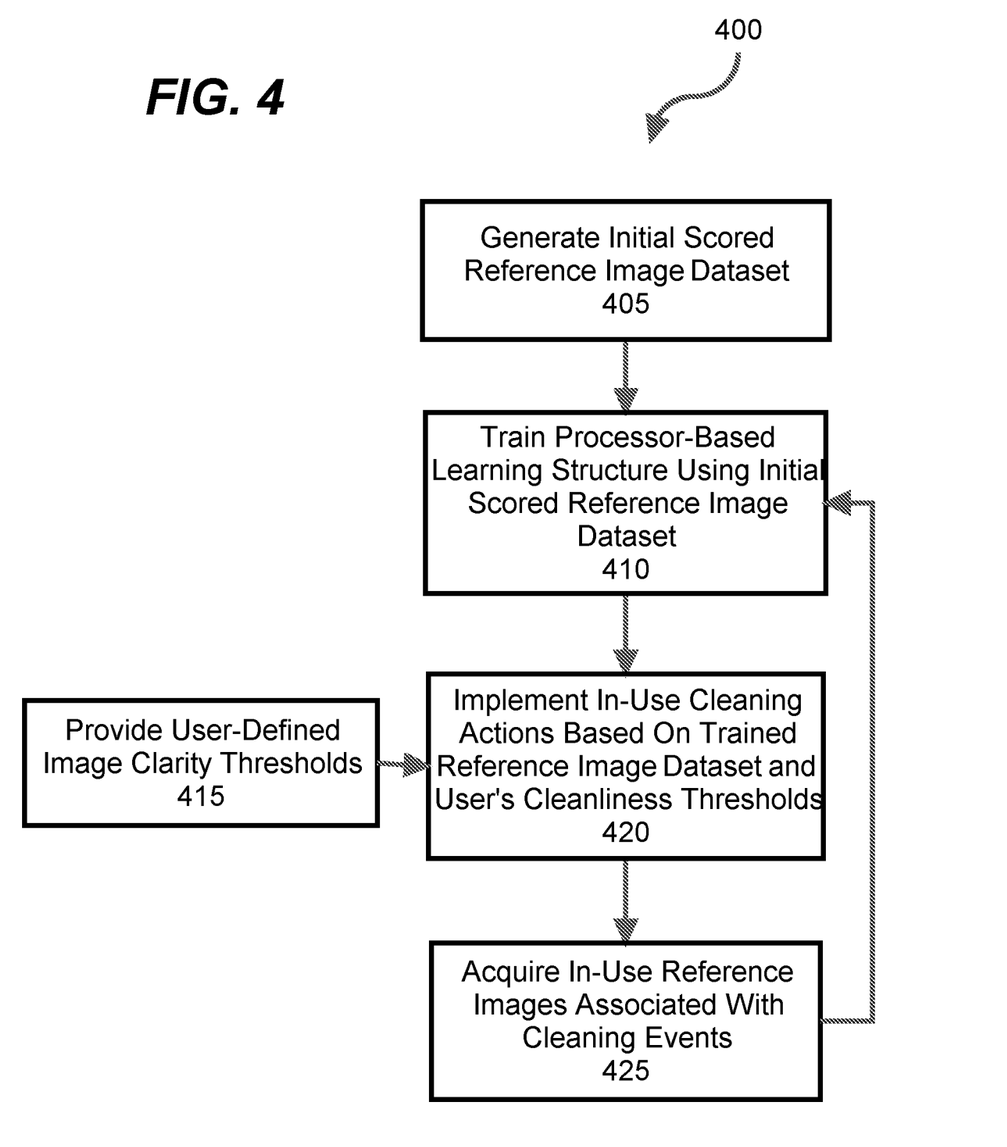
FIG. 4 is a flow diagram view showing a method of implementing responsive actions in accordance with one or more embodiments of the disclosures herein.

Referring now to FIG. 4, a method 400 of implementing in-use responsive actions using a scored reference image dataset created using multiple reference image scoring approaches is shown. At a process 405, an initial scored reference image dataset is provided (e.g., generated). The initial scored reference image dataset may include many images (e.g., 100's 1000's or more) that are each quantitatively scored (e.g., by surgeons, contract scorers, or the like) to indicate a degree of visual clarity—e.g., between 0 for worst visual clarity and 100 for best visual clarity.

At a process 410, the initial scored reference image dataset is used to train (i.e., teach to understand) a processor-based learning structure how to similarly score new reference images that are added to the initial scored reference image dataset to create a current instance of the scored reference image dataset. For example, the initial scored reference image dataset may be used to train a suitably configured a neural network (e.g., a processor-based learning structure) on one or more degrees of clarity—e.g., clean, suitable clean, dirty, etc. As with the initial scored reference image dataset, such training may train the processor-based learning structure to score new reference images in the same manner as which the initial scored reference image dataset was scored—e.g., scored 0 for worst visual clarity and 100 for best visual clarity. To this end, a goal of such training is to teach the system what a video frame (i.e., reference image) should be scored as from 0 to 100. In this respect, the processor-based learning structure may be a neural network or the like used for analyzing, organizing and scoring reference images.

At a process 415, a subset of the current instance of the scored reference image dataset (i.e., including the initial instance) may be used to define one or more visual clarity preferences. For example, to generate a subset of the current instance of the scored reference image dataset, an imaging device user may denote a plurality of reference images of the current instance of the scored reference image dataset as being of a respective degree of clarity—e.g., what the user personally considers to the naked or corrected eyesight to be, for example, suitably clear, unacceptably blurry, dirty etc. This denoted visual clarity preference in conjunction with the reference image database can then be used during a procedure using an imaging device to assess images acquired in a real-time manner during the procedure.

At a process 420, during a procedure using an imaging device (or suitably similar imaging device), responsive actions as related to cleaning of the imaging element of the imaging device are determined. These responsive actions may be determined based upon the current instance of the scored reference image dataset and the one or more user-defined visual clarity preferences. In this manner, this assessment enables images acquired in a real-time manner using the imaging device to be used for determining the responsive actions as related to cleaning the imaging element. Advantageously, the user-defined one or more visual clarity preferences enable the assessment to be customized on a user-by-user basis.

Responsive actions may be implemented in any number of manners. Responsive actions may relate to automated actuation of a cleaning device for cleaning the imaging element, may relate to presentation (e.g., audible, visual or both) of information enabling a user to make a determination as to manual actuation of the cleaning device, or may relate to both. The objective of the responsive actions is to either autonomously actuate the cleaning device for causing the imaging element to be cleaned or convey information to a user of the imaging device for enabling the user to make a determination as to whether or not the imaging element needs to be cleaned (i.e., via manual ex-vivo cleaning or device-based in-vivo cleaning). In one or more embodiments, the responsive action may include a "manual override" (e.g., user causes actuation instance of cleaning device ahead of an autonomous system-determined instance being performed) or "time-delay" option (e.g., system performing cleaning instances upon a designated time-delay intervals with or without any image processing).

In the case of autonomously actuation of the cleaning device, the responsive action may be transmission of an actuation (i.e., control) signal that is transmitted for reception by the cleaning device for causing its actuation to thereby clean the imaging element. The actuation signal may be transmitted in response to a determination being made that visual clarity of one or more reference images corresponds to an unacceptable degree of cleanliness for the imaging element (e.g., via reference to a user-defined visual clarity preference). For example, in response to assessment of one or more images acquired in real-time during a procedure (e.g., a surgical procedure) indicating unacceptable level of cleanliness of the imaging element, the actuation signal is generated and transmitted for reception by the cleaning device to cause its actuation after or upon receipt of the actuation signal.

In the case of information being conveyed to a user of the imaging device for enabling the user to make a determination as to whether or not the imaging element needs to be cleaned, the responsive action may be transmission of a signal that causes cleanliness or clarity representing information to be outputted on a content output device (e.g., a visual display device and audio output device or the like). In some embodiments, the signal represents a score derived as a function of visual clarity of images acquired via an imaging element in real-time during a current procedure and reference images (e.g., images from a scored reference image database).

At a process 425, in response to a cleaning event of the imaging element being detected, one or more new reference images are acquired via the imaging device through the imaging element. For example, prior to each instance of cleaning the imaging element, one or more images can be obtained (e.g., having been stored in memory during the procedure and accessed therefrom) and added as new reference images to create an updated current instance of the scored reference image dataset. In this respect, new reference images can be created and learned each time an imaging device is used in the method 400. Advantageously, new reference images generated in the context with a particular user may be added to that particular user's subset of the scored reference image dataset, thereby further customizing the subset of the user.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A computer-assisted system, comprising:
    an imaging device having an imaging element through which image information of an anatomical structure within a body cavity is acquired during a surgical procedure;
    a cleaning device attached to the imaging device, wherein the cleaning device is adapted to clean a surface of the imaging element in response to activation thereof; and
    one or more processors coupled to the imaging device and the cleaning device, wherein the one or more processors are configured to:
        process a portion of the image information to determine cleanliness of the imaging element; and
        after a determination of the imaging element exhibiting unacceptable cleanliness is made, cause the cleaning device to perform one or more instances of an imaging element cleaning operation, wherein:
    the portion of the image information includes an image of the anatomical structure within the body cavity;
    the one or more processors being configured to process the portion of the image information includes the one or more processors being configured to correlate the image to one or more visual clarity scored reference images each having a respective visual clarity determined to be visually equivalent to the image; and
    each of said scored reference images has a score one of rating cleanliness of an imaging element used for acquiring a respective one of said reference images and ranking cleanliness of an imaging element used for acquiring a respective one of said reference images.

2. The computer-assisted system of claim 1 wherein the one or more processors being configured to process the portion of the image information includes the one or more processors being configured to one of quantitatively characterize cleanliness of the imaging element based at least partially upon the portion of the image information and qualitatively characterize cleanliness of the imaging element based at least partially upon the portion of the image information.

3. The computer-assisted system of claim 1 wherein:
    the computer-assisted system further comprises a visual display device;
    the one or more processors being configured to process the portion of the image information includes the one or more processors being configured to:
        correlate visual clarity of the portion of the image information to one or more visual clarity scored reference images; and
        based at least partially on the score of one or more of said correlated reference images, determine a metric characterizing cleanliness of the imaging element; and
    the one or more processors are further configured to cause the metric to be displayed on the visual display device.

4. The computer-assisted system of claim 1 wherein:
    the computer-assisted system further comprises a visual display device; and
    the one or more processors are further configured to cause a visual indictor characterizing cleanliness of the imaging element to be displayed on the visual display device in response to a determination of the imaging element exhibiting unacceptable cleanliness being made.

5. The computer-assisted system of claim 1 wherein:
    the one or more processors are further configured to enable a particular user of the imaging device to select one or more visual clarity reference images exhibiting acceptable visual clarity; and
    the one or more processors being configured to process one or more of the image information includes the one or more processors being configured to use said selected visual clarity reference images to determine when the imaging element exhibits unacceptable cleanliness for the particular user.

6. The computer-assisted system of claim 1 wherein the one or more processors being configured to cause the cleaning device to perform one or more instances of an imaging element cleaning operation includes the one or more processors being configured to transmit one or more actuation signals for reception by the cleaning device.

7. The computer-assisted system of claim 1 wherein:
    the computer-assisted system further comprises a visual display device; and
    the one or more processors being configured to cause the cleaning device to perform one or more instances of an imaging element cleaning operation includes the one or more processors being configured to:
        issue a request for approval to initiate cleaning of the imaging element by the cleaning device; and
        in response to receiving approval to the request, actuate the cleaning device.

8. The computer-assisted system of claim 1 wherein:
    the computer-assisted system further comprises a visual display device; and
    the one or more processors are further configured to cause a visual indictor characterizing cleanliness of the imaging element to be displayed on the visual display device in response to a determination of the imaging element exhibiting unacceptable cleanliness being made.

9. The computer-assisted system of claim 8 wherein the one or more processors being configured to cause the cleaning device to perform one or more instances of an imaging element cleaning operation after a determination of the imaging element exhibiting unacceptable cleanliness is made includes the one or more processors being configured to enable the operation of the cleaning device to be selectively actuated in conjunction with the visual indicator being displayed.

10. The computer-assisted system of claim 9 wherein:
    the one or more processors are further configured to enable a particular user of the imaging device to select one or more visual clarity reference images exhibiting acceptable visual clarity; and
    the one or more processors being configured to process one or more of said real-time images includes using said selected visual clarity reference images to determine when the imaging element exhibits unacceptable cleanliness for the particular user.

11. The computer-assisted system of claim 9 wherein:
the computer-assisted system further comprises a visual display device; and
the one or more processors being configured to cause the cleaning device to perform one or more instances of an imaging element cleaning operation includes the one or more processors being configured to:
   issue a request for approval to initiate cleaning of the imaging element by the cleaning device; and
   in response to receiving approval to the request, actuate the cleaning device.

12. A robotic surgical system, comprising:
an imaging apparatus including an imaging device and a cleaning device, wherein the imaging device comprises an imaging element for acquiring image information from a surgical field within a body cavity during a surgical procedure and wherein the cleaning device is adapted to clean a surface of the imaging element in response to activation thereof while the imaging element is within the body cavity; and
a control console including a visual display device adapted to have the image information displayed thereon;
a processing unit coupled to the imaging apparatus and the control console, wherein the processing unit comprises one or more processors configured to:
   process a portion of the image information to determine when the imaging element exhibits unacceptable cleanliness; and
   in response to a determination that the imaging element exhibits unacceptable cleanliness, cause one or more responsive actions to be performed by at least one of the cleaning device and the imaging apparatus controller, wherein each of said responsive actions at least one of cause the cleaning device to clean the imaging element through use of at least one of the cleaning device and the visual display device and enable the cleaning device to clean the imaging element through use of at least one of the cleaning device and the visual display device, wherein:
the portion of the image information includes an image of the anatomical structure within the body cavity;
the one or more processors being configured to process the portion of the image information includes the one or more processors being configured to correlate the image to one or more visual clarity scored reference images each having a respective visual clarity determined to be visually equivalent to the image; and
each of said scored reference images has a score one of rating cleanliness of an imaging element used for acquiring a respective one of said reference images and ranking cleanliness of an imaging element used for acquiring a respective one of said reference images.

13. The robotic surgical system of claim 12 wherein said responsive actions include actuating the cleaning device, displaying an indicator of cleanliness of the imaging element on the visual display device and enabling operation of the cleaning device to be selectively actuated.

14. The robotic surgical system of claim 12 wherein the one or more processors being configured to cause one or more responsive actions to be performed includes the one or more processors being configured to:

enable operation of the cleaning device to be selectively initiated by displaying a user-selectable actuation command graphic displayed on the visual display device; and
cause the cleaning device to be actuated in response to selection of the user-selectable command graphic.

15. The robotic surgical system of claim 14 wherein the one or more processors being configured to cause the cleaning device to be actuated in response to selection of the user-selectable command graphic includes the one or more processors being configured to generate an actuation signal and transit the actuation signal for reception by the cleaning device.

16. The robotic surgical system of claim 15 wherein the one or more processors being configured to cause the actuation signal to be transmitted therefrom for reception by the cleaning device includes the one or more processors being configured to generate the actuation signal.

17. The robotic surgical system of claim 12 wherein the one or more processors being configured to cause one or more responsive actions to be performed includes the one or more processors being configured to cause an actuation signal to be transmitted for reception by the cleaning device.

18. The robotic surgical system of claim 12 wherein the one or more processors being configured to process the portion of the image information includes the one or more processors being configured to one of quantitatively characterize cleanliness of the imaging element based at least partially upon the portion of the image information and qualitatively characterize cleanliness of the imaging element based at least partially upon the portion of the image information.

19. The robotic surgical system of claim 12 wherein:
the one or more processors being configured to process the portion of the image information includes the one or more processors being configured to:
   correlate visual clarity of the portion of the image information to one or more visual clarity scored reference images; and
   based at least partially on the score of one or more of said correlated reference images, determine a metric characterizing cleanliness of the imaging element; and
the one or more processors are further configured to cause the metric to be displayed on the visual display device.

20. The robotic surgical system of claim 12 wherein the one or more processors are further configured to cause a visual indictor characterizing cleanliness of the imaging element to be displayed on the visual display device in response to a determination of the imaging element exhibiting unacceptable cleanliness being made.

21. The robotic surgical system of claim 12 wherein:
the one or more processors are further configured to enable a particular user of the imaging device to select one or more visual clarity reference images exhibiting acceptable visual clarity; and
the one or more processors being configured to process one or more of the image information includes the one or more processors being configured to use said selected visual clarity reference images to determine when the imaging element exhibits unacceptable cleanliness for the particular user.

22. A non-transitory machine-readable medium comprising a plurality of machine-readable instructions which when executed by one or more processors associated with a computer-assisted system are adapted to cause the one or more processors to perform a method comprising:

receiving image information depicting an anatomical structure within a body cavity of a surgical patient, wherein the image information is acquired by an imaging element of an imaging device having a cleaning device attached thereto and wherein actuation of the cleaning device causes the cleaning device to perform one or more instances of an imaging element cleaning operation;

deriving, from a portion of the image information, information characterizing cleanliness of the imaging element, wherein deriving said cleanliness characterizing information includes correlating the portion of the image information to one or more visual clarity scored reference images each having a respective visual clarity determined to be visually equivalent to the portion of the image information and wherein each of said scored reference images has a score one of rating cleanliness of an imaging element used for acquiring a respective one of said reference images and ranking cleanliness of an imaging element used for acquiring a respective one of said reference images; and in response said cleanliness characterizing information indicating that the imaging element exhibits unacceptable cleanliness, causing one or more responsive actions to be performed, wherein the responsive actions include:

actuating the cleaning device;

outputting a signal enabling an indicator of cleanliness of the imaging element to be displayed on a visual display device; and enabling operation of the cleaning device to be selectively actuated.

23. The non-transitory machine-readable medium of claim 22 wherein the one or more processors being configured to cause one or more responsive actions to be performed includes the one or more processors being configured to:

enable operation of the cleaning device to be selectively initiated by displaying a user-selectable actuation command graphic displayed on a visual display device coupled to the imaging device; and cause the cleaning device to be actuated in response to selection of the user-selectable command graphic.

24. The non-transitory machine-readable medium of claim 23 wherein the one or more processors being configured to cause the cleaning device to be actuated in response to selection of the user-selectable command graphic includes the one or more processors being configured to generate an actuation signal and transit the actuation signal for reception by the cleaning device.

25. The non-transitory machine-readable medium of claim 22 wherein the one or more processors being configured to cause one or more responsive actions to be performed includes the one or more processors being configured to cause an actuation signal to be transmitted for reception by the cleaning device.

26. The non-transitory machine-readable medium of claim 22 wherein the one or more processors being configured to process the portion of the image information includes the one or more processors being configured to one of quantitatively characterize cleanliness of the imaging element based at least partially upon the portion of the image information and qualitatively characterize cleanliness of the imaging element based at least partially upon the portion of the image information.

27. The non-transitory machine-readable medium of claim 22 wherein:

the one or more processors being configured to process the portion of the image information includes the one or more processors being configured to:

correlate visual clarity of the portion of the image information to one or more visual clarity scored reference images; and based at least partially on the score of one or more of said correlated reference images, determine a metric characterizing cleanliness of the imaging element; and the one or more processors are further configured to cause the metric to be displayed on the visual display device.

28. The non-transitory machine-readable medium of claim 22 wherein the one or more processors are further configured to cause a visual indictor characterizing cleanliness of the imaging element to be displayed on the visual display device in response to a determination of the imaging element exhibiting unacceptable cleanliness being made.

* * * * *